United States Patent [19]
O'Neil

[11] Patent Number: 5,827,353
[45] Date of Patent: Oct. 27, 1998

[54] PRECOLUMN SEPARATOR FOR GAS CHROMATOGRAPH

[76] Inventor: Gregory G. O'Neil, 1872 Bird Rd. P.O. Box 560, Independence, Ky. 41051

[21] Appl. No.: 817,914
[22] PCT Filed: Sep. 6, 1996
[86] PCT No.: PCT/US96/14289
  § 371 Date: Apr. 15, 1997
  § 102(e) Date: Apr. 15, 1997
[87] PCT Pub. No.: WO97/10888
  PCT Pub. Date: Mar. 27, 1997
[51] Int. Cl.⁶ .................................................... B01D 15/08
[52] U.S. Cl. .................................................. 95/87; 96/101
[58] Field of Search .................................. 95/82, 86–89; 96/101, 104–106

[56] References Cited

U.S. PATENT DOCUMENTS

| | | | |
|---|---|---|---|
| 3,063,286 | 11/1962 | Nerheim | 96/105 X |
| 3,225,521 | 12/1965 | Burow | 95/86 |
| 3,881,892 | 5/1975 | Gehrke et al. | 95/86 |
| 4,035,168 | 7/1977 | Jennings | 96/105 X |
| 4,422,860 | 12/1983 | Feinstein | 95/89 X |
| 4,704,141 | 11/1987 | Krebber | 96/106 X |
| 4,805,441 | 2/1989 | Sides et al. | 95/87 X |
| 5,057,126 | 10/1991 | Lubkowitz et al. | 96/104 X |
| 5,096,471 | 3/1992 | Sacks et al. | 96/105 X |
| 5,288,310 | 2/1994 | Peters et al. | 96/105 X |
| 5,588,988 | 12/1996 | Gerstel et al. | 96/105 X |

FOREIGN PATENT DOCUMENTS 1-176942  7/1989  Japan ........................................ 96/101

*Primary Examiner*—Robert Spitzer

[57] ABSTRACT

A precolumn separator provides a method of separating a solvent from a sample for use in a gas chromatograph. The precolumn has an independent carrier gas control mechanism which allows the carrier gas to be passed through the preseparation column at a rate favorable for stripping the solvent from the sample. The solvent-laden carrier gas is then purged through a purge vent which is separate from the gas chromatograph. After a period of time which effectively permits the carrier gas to be significantly removed from the sample, the flow rate of the carrier gas is reduced to the normal operating gas flow rate and the purge vent is closed. The sample is then passed through the column to the gas chromatographic column. A second purge vent can then be directed to the purge vent inlet in the gas chromatograph. Preferably, the preseparation column is a packed column which includes a separate heating element. The heating element, in turn, can be surrounded by an air cooled jacket. The air cooled jacket has an inlet at the bottom of the preseparation column and a spiral flow path around the heater. This will cause the bottom of the preseparation column to be cooler than the upper portion which, in turn, will cause a compression of the sample near the outlet. This permits stripping of a significant amount of solvent from the sample while, at the same time, eliminating the need to match the sample injection rate to the solvent evaporation rate.

13 Claims, 3 Drawing Sheets

PRECOLUMN SEPARATOR FOR GAS CHROMATOGRAPH

BACKGROUND OF THE INVENTION

Chromatography is a method of separating mixtures of compounds into their components. It enables one to separate trace impurities or major fractions from each other. These separated components can then be analyzed by various methods, including spectrographic methods.

Chromatography is based on the separation of different types of molecules as they pass down along a column which contains material that exhibits attractive selectivity for certain compounds. The column may be packed with a material that provides a high surface area or a wall coated film, and that interacts physically with the compounds being analyzed. The packing or wall coated film of inert material acts as a stationary phase. As the sample passes along the column, it separates into its different components which can then be characterized and identified. This can also be used to measure how much of each component is present in the mixture.

One particular type of chromatography is gas chromatography. In gas chromatography, the sample is transformed into a gas phase. An inert gas is used as a carrier to propel the sample along the column under constant mass flow rate conditions. The inert gas passes through the chromatographic column at a constant velocity because it does not interact with and therefore spend time on the stationary phase. The sample is injected into the carrier gas and is swept along the chromatographic column. The different substances or analytes within the sample interact differently with the stationary phase, thus taking different times to pass through and exit the column to reach the detector. This permits independent analysis of the analyte components.

In order to provide greater and greater sensitivity, the diameter of the column has been decreased and its length has been increased. Very narrow columns (0.1 mm–0.5 mm internal diameter) are used. These are referred to as capillary columns and they may be several hundred feet long. These are not packed, but rather the inside wall of the column is coated with a selective partitioning material. These allow sample mixtures dissolved in 1 $\mu$l–5 $\mu$l of solvent to be injected and analyzed.

With these capillary column gas chromatographs, the solvent becomes an overwhelming problem. The sample size simply needs to be minimized in order to permit proper separation due to the lower mass loading capacities of these films. Where the substances being detected are at very low concentrations, this can present a problem. There simply may not be enough of the analyte in the solvent to be properly detected.

One way to resolve this issue has been to inject a larger sample and separate the solvent from the sample after it is injected. One particular process is programmed temperature sample introduction, also known as "PTV injection." In PTV injection, the sample with the solvent is injected into a liner which serves as an evaporator chamber. The temperature of the tube can be varied from relatively low temperature causing the sample to remain in the liner, then heated to provide a gas phase mixture which is now concentrated within the range of detection. The carrier gas is introduced through the tube, causing evaporation of the solvent. Generally the solvent is more volatile than the sample and is allowed to be vented into the purge of the gas chromatograph. In order for this to effectively concentrate a sample, the sample must be injected at a rate which matches the solvent evaporation rate. This requires a very expensive programmable injector. Typically, samples are introduced into a gas chromatograph by simply pressing a hypodermic syringe manually. The need to rely on a programmable injector is time-consuming and, in addition, significantly increases capital expenses.

Further, with the PTV apparatus, the purge and the carrier gas flow are not independent of the gas chromatograph. Thus, the purge and carrier gas flow are optimized to meet the requirements of the gas chromatograph. This all has a limiting effect on the amount of solvent that can be split from the sample. The PTV has limited geometry (typically 80 mm in length) and thus cannot serve as a chromatographic device, but as an injection device only.

SUMMARY OF THE INVENTION

The present invention is premised on the realization that an efficient programmable precolumn separator for a gas chromatograph can be provided wherein the gas flow rate and solvent purge are independent of the gas chromatograph. Further, this device may act as a new form of sample introduction by acting as both an injection device and a chromatographic device. This temperature programmable precolumn adds temperature and flow chromatographic selectivity to the injection process. Solvents and other interferences are separated before introduction into the gas chromatographic column. Through the use of time programmable venting and column introduction, a wide variety of selected compounds may be analyzed. This form of sample introduction not only enhances sensitivity via concentration, but also permits selected bands to be analyzed without interferences normally encountered. Further, the environment of a precolumn is more efficient in mass transfer than the traditional liner (borosilicate evaporation chamber), and thus transfers more analyte per microliter than conventional techniques such as PTV and standard splitless injections. Finally, speed of analysis is enhanced through the precolumn introduction of bands which permits the analysis of complex mixtures on shorter length capillary columns leading to faster analysis times.

According to the present invention, the carrier gas flow rate is controlled independently of the gas chromatograph to optimize separation in a precolumn which is preferably a packed precolumn. Further, the purge vent of solvent is also controlled at least partially independently of the gas chromatograph and preferably the majority of the solvent is vented outside of the gas chromatograph, generally to the atmosphere.

In a preferred embodiment of the present invention the precolumn separator includes a packed column surrounded by an independently controlled heater, and a cooling jacket. The sample is injected into the precolumn where it passes through the initial packed column. The carrier gas flow rate is controlled to optimize separation through the precolumn. The sample is split at the bottom of the column, allowing the rapidly evaporated solvent to be vented out the purge vent. The heater surrounding the column and air cooling jacket around the heater enable one to maintain the upper portion of the packed column adjacent the injection port at a higher temperature than the lower discharge portion of the packed column. This will cause compression of the sample as it nears the exit port. A majority of the solvent will be rapidly stripped from the sample so that the vast majority of the sample initially departing the precolumn will be solvent. This will then be followed by condensed bands of analyte and interferences (higher boiling point than the vented solvent). The analyte bands will then pass through the exit port from the precolumn and be directed to the gas chromatograph capillary column and subsequently to the detector while interferences are selectively vented away from the column.

By controlling the flow rate of the carrier, independent of the gas chromatograph, the stripping of the solvent and chromatographic band separation within the precolumn may be optimized. The efficiency of the separation is further improved by utilization of packed or wall coated precolumns with long path lengths (240 mm versus 80 mm standard). The types of precolumn used include single and multistrand wall coated capillaries, as well as packed.

The carrier gas flow rate can be controlled either by a separate purge flow control valve or, alternately, by an electronically-controlled, variable mass flow control valve. The present invention permits significant quantities of solvent to be stripped from a sample, thus permitting a very large sample to be introduced into the gas chromatograph. Further, this does not require that the sample injection rate match the solvent evaporation rate for reliable results. This significantly reduced the time required to run a sample through the gas chromatograph allowing results to be obtained relatively quickly, permitting the gas chromatograph to be used more efficiently. In a preferred embodiment, the heater is an infrared quartz heater which provides extremely rapid heating of the precolumn without communication of its temperature to the gas chromatograph. This heating significantly improves separation efficiency. Other objects and advantages of the present invention will become apparent in light of the following detailed description and drawings in which:

DETAILED DESCRIPTION

The present invention is a precolumn separator 12 for a gas chromatograph 14. The precolumn separator 12 will generally include an injection port 16 coupled to a separation column 18 which has a first outlet 20 which leads to the inlet of the gas chromatograph 14.

Figures 4, 6:
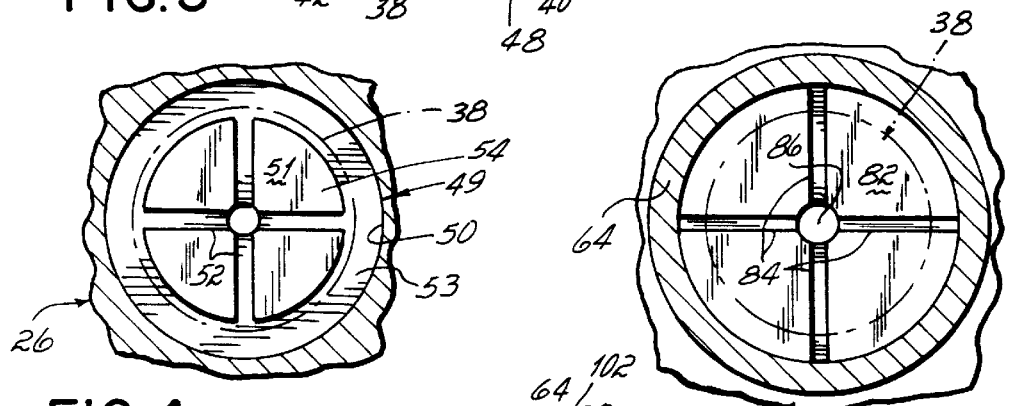
FIG. 4 is a view as seen on line 4—4 of FIG. 3.
FIG. 6 is a view as seen on line 6—6 of FIG. 5.
Figure 5:
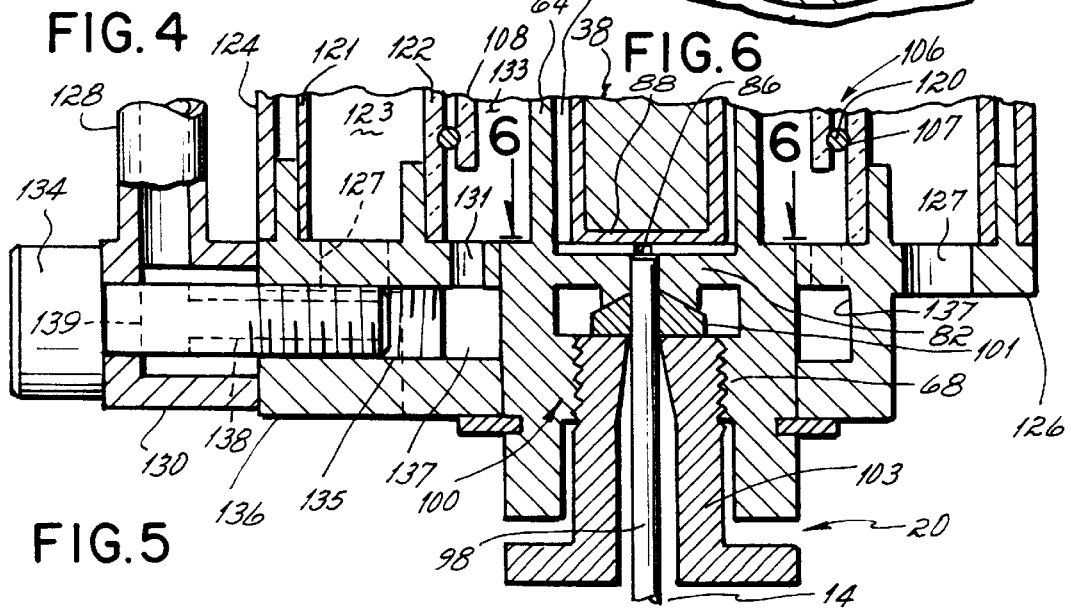
FIG. 5 is an enlarged cross-sectional view of the lower portion of FIG. 2.

The injection port 16 will include a rubber septum 22, as typically employed by a gas chromatograph, which is held in position by a septum nut 24 which screws onto an inlet chamber 26. The inlet chamber 26 includes a carrier gas inlet 28 which leads to an inner portion 30 of the chamber 26. Chamber 26 also includes a septum purge outlet 32. The inner portion of chamber 26 also includes a stepped bore 49. The large diameter portion 50 of this bore has a ceiling area 51 having four radial slots 52 (see FIG. 4) and an annular passage 53. Gas inlet 28 and purge outlet 32 are interconnected via these slots 52 and passage 53, and lead to the head space 54 of packed column 38. The purge inlet, purge outlet, and septum are all part of most gas chromatographs with the chamber 26 supported on the housing 39 of the gas chromatograph by a rectangular bracket 44. Beneath the inner portion 30 of the chamber 26 is an o-ring 34 forming a seal between the outer wall 36 of a packed column 38 and the chamber 26. This separates the inlet chamber 26 and a purge outlet chamber 40. Tube 42 is secured at its first upper end 43 to the chamber 26 by a nut 41 and extends from chamber 40. Tube 42 includes the purge outlet chamber 40 at its first end and has a second externally-threaded end 46.

The packed or wall coated column 38 extends through tube 42 with a space 48 between the packed column 38 and tube 42. Surrounding the tubular extension is an electric heater 60 which is adapted to vaporize the sample when it is injected through the septum 22. This heater is also typically included with many gas chromatographs.

Attached to tube 42 is a black chrome plated metal tube 64 which has an internally threaded first inlet end 66 which is screwed onto the externally threaded second end 46 of tube 42. A seal is formed between the two by a packing ring 61. Tube 64 also includes a second outlet end 68 which is internally threaded. The second outlet end 68 includes a plate portion 82 having horizontal channels 84 and a hole 86 which is connected to the inlet of the gas chromatograph 14.

The packed column 38 extends through metal tube 64 and the end 88 of the packed column rests on plate portion 82. Channels 84 pass beyond the packed column to a gap 102 between the internal wall of the tubular extension 64 and the packed column 38, aligned with space 48 between tube 42 and packed column 38. A hole 86 passes through plate 82 and expands to form a connection 100 for the capillary column 98 of the gas chromatograph. Separation column 98 is fixed to connector 100 using a standard connection—in this case, a graphite packing ring 101, held tight with a threaded fitting 103.

The gaps 102 and 48 extend the length of the packed column and lead to the chamber 40 and eventually to the purge outlet 104.

Surrounding the extension tube 64 is a quartz heater 106. Heater 106 includes an inner cylindrical quartz tube 108 which surrounds the extension tube 64. Tube 108 includes a helical groove 107. A nickel/chromium heating element 120 rests in groove 107 and is connected to electrical leads 119. The nickel/chromium heating element 120, in turn, is surrounded by a second quartz tube 122. A third quartz tube 121, having sputter deposited gold inner and outer surfaces, surrounds tube 122 with a space 123 separating the two. Temperature sensors can be located anywhere along the tube 64, as desired. Surrounding the tube 121 is a metal protective sleeve 124. Heater 106 and tube 121 and protective sleeve 124 are supported at their upper ends by cap 125, and at their lower ends by manifold cap 126.

Manifold cap 126 includes a first series of holes 127 which lead into space 123. In turn, cap 125 includes a series of radial slots 129, which intersect with space 123. This allows air to passively flow from holes 127 through space 123 out slots 129.

Cap 126 also includes a second series of holes 131 which lead to space 133 between heater tube 108 and tube 64. Holes 131 connect space 133 to a manifold 136 which has an annular passage 137 leading to another internally-threaded inlet 135.

A cooling gas tube 128 having an annular sleeve 130, is attached to inlet 135 by a screw 134. Screw 134 has an axial bore 138 which intersects a radial second bore 139. Annular sleeve 130 has a stepped diameter. Its inner threaded portion is larger than its outer portion. The large diameter inner portion permits air flow from tube 128 into screw 134 through bore 139 into axial bore 138 and into the annular passage 137 of manifold 136. A pump 210 (FIG. 1) can actively force a heat exchange fluid through the space 133 to cool or heat heater 106. Space 133 also intersects with slots 129 to permit cooling air to exit.

Figure 1:
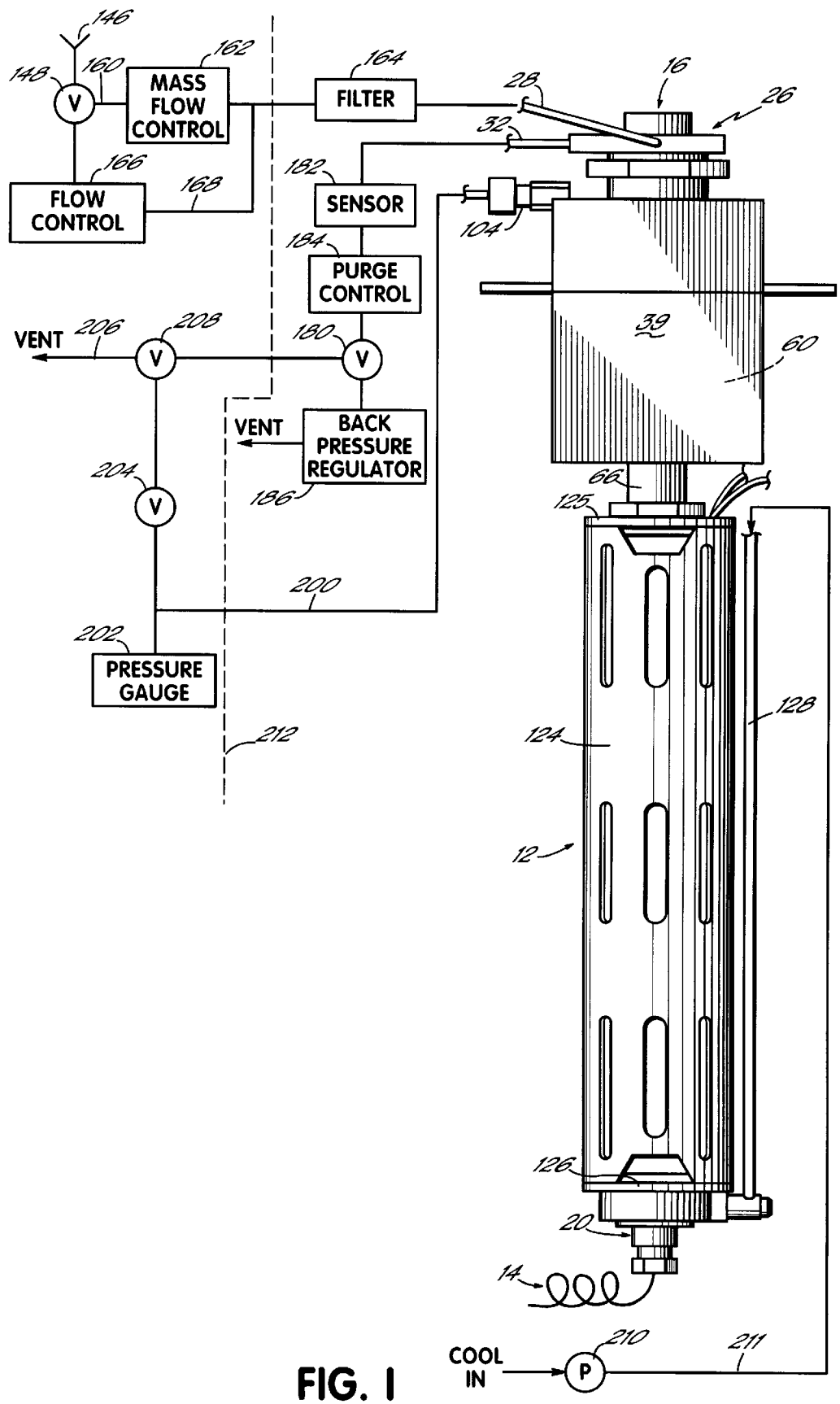
FIG. 1 is a diagrammatic depiction of a gas chromatograph in combination with a precolumn separator of the present invention.

As shown more particularly in FIG. 1, the gas chromatographic system will generally include a source of carrier gas 146 which will, in turn, lead to a flow select valve 148. This flow select valve 148 includes a normally open carrier out line 160 which leads to the mass flow control valve 162 of the gas chromatograph, which in turn leads to a filter 164 and to the carrier gas inlet 28 into inlet chamber 26. The flow select valve 148 has a second line (normally closed) which, when opened, leads to a purge flow control 166, which in turn leads to purge line 168, which also leads to filter 164 and in turn directs the carrier into the carrier inlet 28.

The septum purge outlet 32 of chamber 26 leads to solenoid valve 180 which vents the septum purge. This may also include a sensor 182 and a septum purge control 184 as well as a back-pressure regulator 186. The solenoid valve 180 may lead to a line to the vent select valve 208, as described below.

In this system, the mass flow control valve 162, as well as the filter 164, solenoid valve 180 with the attendant sensor 182 and regulator 186, are all portions of the gas chromatograph and are internal to the gas chromatograph but are shown diagrammatically here for illustration purposes separated by dashed line 212.

Figure 2:
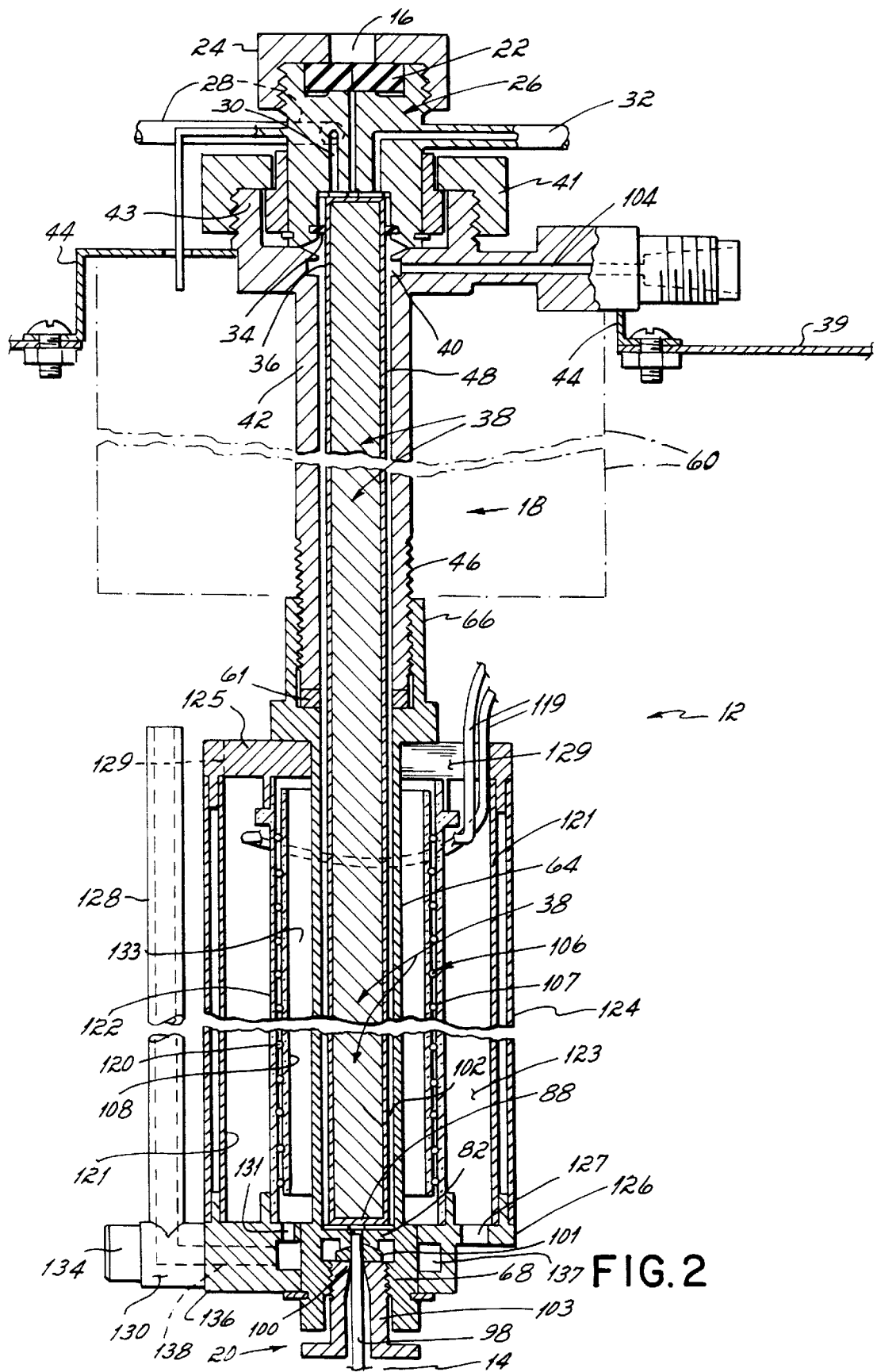
FIG. 2 is a cross-sectional view of the precolumn separator of the present invention.
Figure 3:
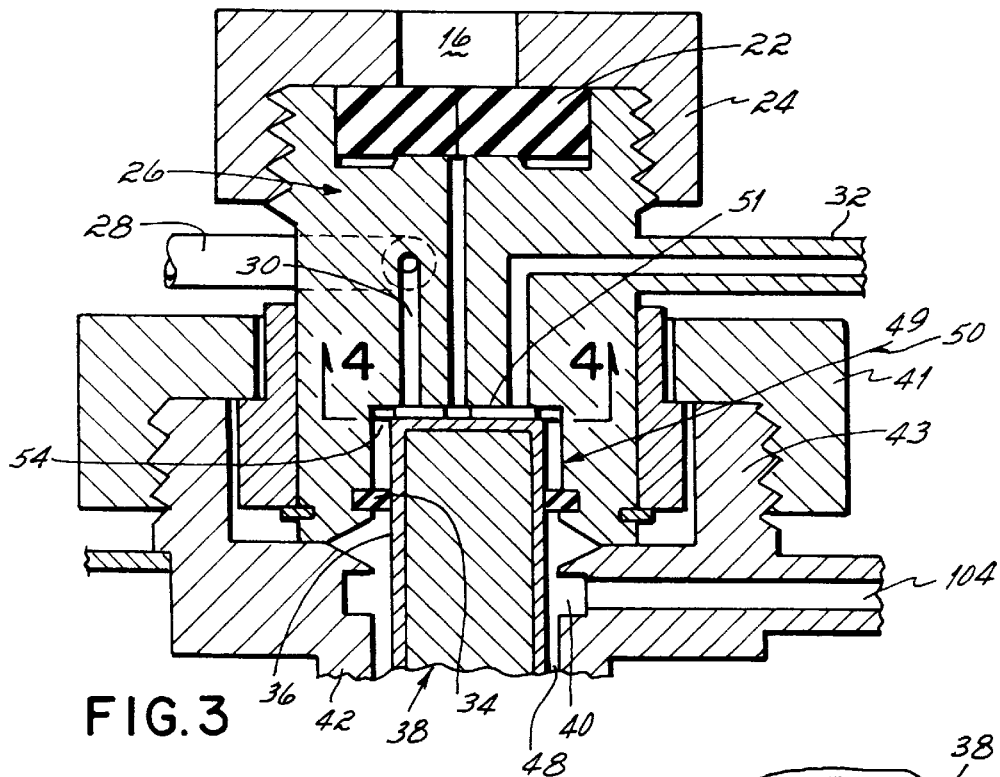
FIG. 3 is an enlarged cross-sectional view of the upper portion of FIG. 2.

The split purge outlet from purge outlet chamber 40 (FIG. 2) extends to a split purge line 200, which will in turn lead to a vent shut-off valve 204, leading to the vent select valve 208 and in turn to a purge vent 206. The pressure of this can all be regulated by a system pressure gauge 202.

Finally, the separation column includes a cooling air pump 210 which leads, via line 211, to the inlet tube 128 to the annular chamber 137 for the cooling jacket or spaces 132, 133 for heater 106.

For operational purposes, the heater 60 is an aluminum block heater which is part of the standard gas chromatograph. This generally can be heated from room temperature to 450° C. with a heating rate of up to 120° per minute, depending on the particular unit. The quartz heater 106, in turn, will have a heating capacity of room temperature up to about 800° C. with a heating rate of 1–360 degrees per minute in the range of 50°–800° C. In turn, the cooling air will provide for a cooling rate of about 1°–300° C. per minute.

In operation, a sample, generally about 10 to 50 μl, will be injected through injection port 16. It will be preheated by preheater 60. Carrier gas will be introduced through inlet 28 into chamber 26 and a small portion (less than 10%) will be allowed to flow through the purge line 32, controlled by the septum purge control 184. The sample, which enters chamber 26, will be quickly vaporized by heater 60, which will initially flash off the solvent. The solvent will be directed through packed column 38. The packing in the column can be any standard packing for a gas chromatograph. Typical packings could include OV17, OV5, OV1, mole sieves, or wall coatings of various polarities. Also, the tube can be filled with a series of coated microcolumns. The diameter of the packed column will be from about 0.4 mm to about 5 mm. This can be varied, depending upon the particular apparatus to which this is attached. The gas flow through line 28 will continue to force the solvent in advance of the analyte through the packed column. Once the solvent and analyte leave the tube 66, they will enter the portion of tube 38 surrounded by heater 106. Heater 106, being a quartz heater, will be rapidly heated. Cooling air will be introduced through line 128 which will act to maintain the lower portion of the packed column at a temperature lower than the upper portion of the packed column. The solvent will quickly pass through the column, as it is generally significantly more volatile than the analyte. Pressure gauge 202 will allow the solvent portion to be vented through line 104 and 200 and discarded. Pressure gauge 202 will then close line 206, which will, in turn, force the carrier gas passing through column 38, along with the analyte, to continue down the column toward column portion 14 of the gas chromatograph. Since cooling gas enters through the bottom of the heater, the bottom of the packed column is actually cooler than the top. This change in temperature will then cause the analyte, which has been separating as it passes through the packed column, to compress. Thus, as it enters the separation column 14, it will enter as a compressed sample which will provide for more reliable and consistent separations. Since the majority of the solvent is vented off, a larger amount of analyte can be added to the column. Further, the elimination of the solvent will reduce noise, providing for clearer peaks.

The gas chromatograph of the present invention can also be used in a variety of different manners. One option is to inject with low temperature in heater 60, which would, in turn, permit the sample to be injected cold onto the precolumn separator 12. This would have the following advantages: large geometry, temperature programmability, on-column (precolumn) injections for thermally sensitive compounds. Further, the present apparatus can be used without the heater and actually cooling fluid can be introduced through line 211 to provide a cool on-the-column separation. By independently controlling the solvent purge, along with the beating/cooling parameters along the precolumn 38, a wide variety of different separation techniques can be employed to accomplish different features. Thus, the present invention not only facilitates precise separation of analyte, allowing for significantly better resolution and, in turn, interpretation through mass spectrophotometer and the like, it is extremely flexible, permitting a wide variety of different applications.

The preceding has been a description of the present invention, along with the preferred method of practicing the present invention currently known. However, the invention itself should be defined by the appended claims wherein we claim:

1. A method of stripping solvent from a sample and passing said sample through a gas chromatograph, said method comprising adding said sample to a precolumn, mixing said sample with a carrier gas flowing at a first flow rate into said precolumn whereby said carrier gas flows through said precolumn carrying said sample with said carrier gas;

venting a first portion of said sample through a purge vent to an area outside of said gas chromatograph;

decreasing said carrier gas flow rate to a second flow rate directing a portion of said sample from said precolumn to a detector and a second portion of said sample to a purge inlet in said gas chromatograph.

2. The method claimed in claim 1 wherein said precolumn is heated.

3. The method claimed in claim 1 wherein an upper portion of said precolumn is heated to a higher temperature than a lower portion of said precolumn.

4. A precolumn separator for a capillary gas chromatograph comprising a sample inlet, a carrier gas inlet, said inlets leading to a separation column, said separation column having a first end and a second end, said second end directed to a first and second outlet, said first outlet directed to an inlet of a gas chromatograph, said second outlet directed to a purge control valve, said purge control valve having an opening directed separate from said gas chromatography;

and a gas flow control adapted to establish a first gas flow to strip solvent from a sample injected into said separator and a second flow rate to carry sample through said column after a portion of said solvent has been stripped from said sample.

5. The apparatus claimed in claim 4 wherein said separation column is at least partially surrounded by a heater.

6. The apparatus claimed in claim 5 wherein said heater is in turn surrounded by a cooling jacket having a coolant inlet and a coolant outlet, wherein said coolant inlet is adjacent a bottom end of said apparatus and said coolant outlet is adjacent said sample inlet.

7. The apparatus claimed in claim 6 wherein said heater is programmable over a period of time.

8. The apparatus claimed in claim 7 further comprising an air pump adapted to inject cooling air into a bottom portion of said cooling jacket.

9. The apparatus claimed in claim 8 further comprising a first and second purge vent, said first purge directed to said purge control valve, and wherein said second purge vent is directed toward a purge inlet into said gas chromatograph.

10. A gas chromatographic apparatus having a precolumn separator in combination with a gas chromatographic column and a detector, a sample injection port into said precolumn separator, and a carrier gas into said precolumn separator, wherein said carrier gas is controlled by a programmable variable control valve, a first purge directed to said gas chromatograph, and a second purge which is vented outside of said gas chromatograph, whereby said variable carrier gas control valve can be adjusted at a first high rate to direct solvent in a sample through said precolumn separator and out said second purge line and said carrier gas can be reduced to a second flow rate when said second purge line is closed to direct sample to said gas chromatographic column.

11. The apparatus claimed in claim 10 wherein said precolumn separator has a heater.

12. The apparatus claimed in claim 11 wherein said heater is variable to have a first temperature at a first portion of said precolumn and a second temperature at a second portion of said precolumn.

13. The apparatus claimed in claim 10 wherein said precolumn further includes a cooling jacket with a cooling fluid inlet and outlet.

* * * * *

UNITED STATES PATENT AND TRADEMARK OFFICE
CERTIFICATE OF CORRECTION

PATENT NO. : 5,827,353
DATED : October 27, 1998
INVENTOR(S) : Gregory G. O'Neil

It is certified that error appears in the above-identified patent and that said Letters Patent is hereby corrected as shown below:

In Column 7, lines 6-7, delete "chromatography" and insert --chromatograph--

Signed and Sealed this

Twenty-fifth Day of April, 2000

Attest:

Attesting Officer

Q. TODD DICKINSON

Director of Patents and Trademarks